US012569151B2

(12) United States Patent
Ringelstein et al.

(10) Patent No.: US 12,569,151 B2
(45) Date of Patent: Mar. 10, 2026

(54) SYSTEM FOR MONITORING AN OCCUPANT OF A MOTOR VEHICLE

(71) Applicant: VALEO COMFORT AND DRIVING ASSISTANCE, Créteil (FR)

(72) Inventors: Nicolas Ringelstein, Créteil (FR); Frederic Autran, Créteil (FR)

(73) Assignee: VALEO COMFORT AND DRIVING ASSISTANCE, Créteil (FR)

( * ) Notice: Subject to any disclaimer, the term of this patent is extended or adjusted under 35 U.S.C. 154(b) by 140 days.

(21) Appl. No.: 18/284,034

(22) PCT Filed: Mar. 14, 2022

(86) PCT No.: PCT/EP2022/056533
§ 371 (c)(1),
(2) Date: Sep. 25, 2023

(87) PCT Pub. No.: WO2022/200102
PCT Pub. Date: Sep. 29, 2022

(65) Prior Publication Data
US 2024/0164652 A1      May 23, 2024

(30) Foreign Application Priority Data

Mar. 25, 2021      (FR) ...................................... 2103023

(51) Int. Cl.
*A61B 5/024*          (2006.01)
*A61B 5/00*          (2006.01)
(52) U.S. Cl.
CPC ........ *A61B 5/02416* (2013.01); *A61B 5/6893* (2013.01)
(58) Field of Classification Search
None
See application file for complete search history.

(56) References Cited

U.S. PATENT DOCUMENTS

2016/0198147 A1 * 7/2016 Waligorski .............. G01S 17/36
348/49
2017/0353672 A1 * 12/2017 Nakamura ........... A61B 5/4064
(Continued)

OTHER PUBLICATIONS

Gonzalez-Banos H et al. "Computing depth under ambient illumination using multi-shuttered light" Proceedings of the 2004 IEEE Computer Society Conference On Computer Vision and Pattern Recognition, Jun. 27-Jul. 2, 2004, Washington, DC, USA, IEEE, Proceedings of the 2004 IEEE Computer Society Conference on Computer vision and Pattern Recognition IEE, vol. 2, Jun. 27, 2004 (Jun. 27, 2004), pp. 234-241, DOI: 10.1109/CCVPR.2004.1315169, ISBN: 978-0-7695-2158-9. XP010708658 (8 pages).
(Continued)

*Primary Examiner* — Katherine L Fernandez
(74) *Attorney, Agent, or Firm* — Osha Bergman Watanabe & Burton LLP

(57)          ABSTRACT

The monitoring system (1) comprises:
   a light source (3),
   an image acquisition device (5) comprising a shutter (11) which allows light to pass during a period (P1) when the source is active and during a period (P2) when the source is inactive, the light received by a sensor (9) comprising a component (Ca) due to ambient illumination and a component (Ci) due to the light source;
   a processing unit (7) configured for determining a physiological parameter of the occupant by photoplethysmography.
The shutter (11) allows light to pass during a third period (P3), said light comprising the component (Ca) due to ambient illumination and the processing unit (7) being configured for subtracting this component (Ca) from the light received (9) during the other two periods for the purpose of isolating the component (Ci) due to the source in acquired images.

10 Claims, 6 Drawing Sheets

(56)                     References Cited

U.S. PATENT DOCUMENTS

2018/0191936 A1      7/2018  Wang et al.
2020/0297270 A1*    9/2020  Ando ..................... A61B 5/363

OTHER PUBLICATIONS

International Search Report and Written Opinion in corresponding
International Application No. PCT/EP2022/056533, dated Jun. 30,
2022 (17 pages).

* cited by examiner

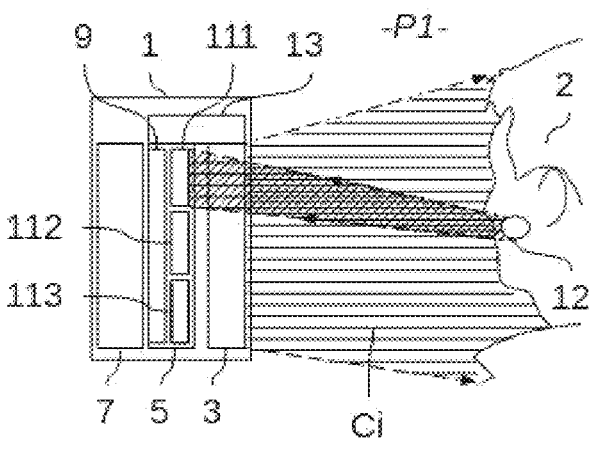
Fig. 6a
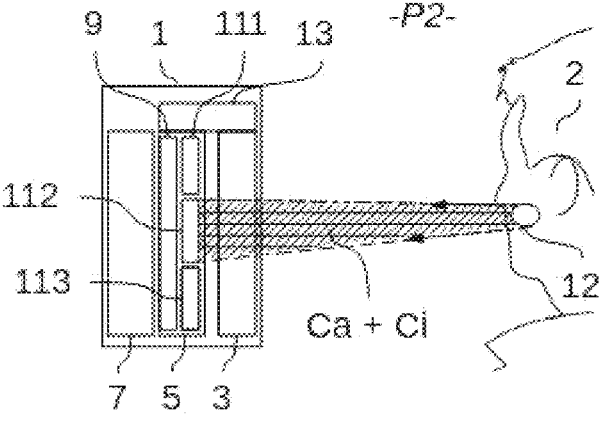
Fig. 6b
Fig. 6c

SYSTEM FOR MONITORING AN OCCUPANT OF A MOTOR VEHICLE

The field of the present invention relates to a system for monitoring an occupant of a motor vehicle. More precisely, the aim of this monitoring system is to determine one or more physiological parameters of an occupant of a motor vehicle by remote photoplethysmography. This monitoring system also has the aim of defining, on the basis of said parameter, the physiological state of said occupant. The invention also relates to a method of determining the physiological state of the occupant by photoplethysmography, this method using said monitoring system.

A person's vital signs, such as the heart rate, the respiratory rate or the arterial blood oxygen saturation may serve as indicators of a person's state of health (also called the "physiological state"). Plethysmography is a method of measuring the changes in volume of part of the body (such as an organ), from which these vital signs can be deduced. Plethysmography is used, notably, to detect changes in volume due to a cardiovascular pulse wave which passes through a subject's body with each heartbeat. The known methods of plethysmography include, notably, photoplethysmography, an optical measurement technique for evaluating a change, variable over time, in the reflectance or transmission of light in an area or region of interest.

Photoplethysmography is based on the fact that blood absorbs more light than the surrounding tissues, and therefore the variations of blood volume generated with each heartbeat affect the transmittance and reflectivity. By evaluating the transmittance and/or reflectivity at different wavelengths (typically red and infrared), the oxygen saturation of the blood or other parameters related to the vital signs of the subject under investigation may be determined. Photoplethysmography may be conducted "remotely", in a non-intrusive way, that is to say without contact with said subject. For this purpose, light sources (notably infrared light sources) and one or more image acquisition devices, image acquisition devices, such as a photographic apparatus or camera, are used, for example. This equipment is thus positioned remotely from the subject during image capture.

Remote photoplethysmography may prove useful in the context of a motor vehicle application for enhancing road safety, notably for monitoring the physiological state of the driver of said motor vehicle. However, changes of illumination in the interior of a motor vehicle, and more particularly drastic changes of illumination on the occupant's face or hands, give rise to difficulties in the acquisition and use of the data by the image acquisition device(s). Indeed, the illumination in the interior is variable over time, depending notably on the external environment of the vehicle (the weather, the presence of buildings or trees or any other object that may create shade, the time at the moment of image acquisition, etc.). If we consider that the light reflected by the driver comprises one component due to the illumination from infrared light sources and another component due to ambient illumination, then clearly the variations of the component due to ambient illumination have significant effect on the light received by the sensor(s) of the image acquisition device(s). The change of illumination on the driver's face is capable of altering the images, limiting the reliability of the data used in the determination of one or more physiological parameters by photoplethysmography. In these conditions, real-time monitoring of the vital signs of the motor vehicle occupant may prove difficult.

Moreover, any light detected by the sensor of the acquisition device generates "shot noise" such that a high value of the component due to ambient illumination decreases the signal to noise ratio and makes it more difficult to detect the useful signal. It is therefore essential to obviate the component due to ambient illumination in the light received by the sensor of the image acquisition device, in order to enhance the reliability of the method of determining a physiological parameter of the motor vehicle occupant by photoplethysmography.

The object of the invention is to at least partially mitigate these drawbacks of the prior art by providing a straightforward, effective and economical solution.

To this end, the invention proposes a system for monitoring an occupant of a motor vehicle, the monitoring system comprising a pulsed light source configured for emitting a train of light pules towards the occupant, an image acquisition device such as a time of flight camera, said image acquisition device comprising an image sensor and a shutter configured for allowing light to pass towards the image sensor during a first acquisition period in which the pulsed light source emits a light pulse and during a second acquisition period in which the pulsed light source is inactive, the second acquisition period being initiated outside the first acquisition period, the respective durations of the first and second acquisition periods being at least equal to the duration of a light pulse emitted by the pulsed light source, the light received by the image sensor in the first acquisition period and the second acquisition period comprising a component due to ambient illumination and a component due to the light pulse emitted by the pulsed light source, the monitoring system further comprising a processing unit configured for determining a physiological parameter of the occupant by photoplethysmography on the basis of the acquired images and for defining the physiological state of the occupant on the basis of said parameter, the monitoring system being characterized in that the shutter is also configured for allowing light to pass towards the image sensor during a third acquisition period initiated outside the first and second acquisition periods, the pulsed light source being inactive during the third acquisition period, said light comprising the component due to ambient illumination, the processing unit being configured for subtracting this component due to ambient illumination from the light received by the sensor during the first and second acquisition periods, for the purpose of isolating the component due to the light pulse emitted by the pulsed light source within some or all of the totality of images acquired by the image acquisition device during the first and second acquisition periods.

Such a monitoring system therefore makes it possible to obviate the variations introduced by the component due to ambient illumination on the images acquired by the image acquisition device(s), thus making it possible to apply the methods of photoplethysmography in order to determine one or more physiological parameters of the occupant for the purpose of evaluating his physiological state. Additionally, the time of flight (ToF) camera makes it possible to acquire information related to the depth and/or the distance: with this kind of camera it is possible to evaluate the distance between the occupant and the image acquisition device, by calculating the time of flight required by the light pulses emitted by the light source for their transit between said light source and the objects filmed and the sensor of the time of flight camera. With such a time of flight camera, therefore, it is also possible to reconstruct the filmed scene (particularly the driver's face, in the present case) in three dimensions in real time. Such a monitoring system can thus allow real-time monitoring of the movements of the occupant, particularly his head, and the selection of the images showing a profile (notably face-on) to be processed by the method of computing the physiological state of the occupant, while suppressing, notably, images considered to be unusable for the purposes of photoplethysmography.

The invention may also comprise one or more of the following aspects, considered in isolation or in combination:

the duration of each of the first, second and third acquisition periods is less than 50 ns, and more particularly equal to 20 ns;

the durations of the first, second and third acquisition periods are identical to each other;

the duration of one pulse of the train of light pulses emitted by the pulsed light source is equal to the duration of the first acquisition period;

the monitoring system comprises a control unit configured for synchronizing the start of the train of light pulses emitted by the pulsed light source with the opening of the shutter at the start of the first acquisition period;

the control unit is configured for controlling the opening and closing of the shutter;

the monitoring system is configured for selecting a region of interest on the occupant's face to enable the physiological parameter to be determined;

the image sensor is configured for producing a depth map of the occupant's face on the basis of the images acquired by the image acquisition device;

the image acquisition device comprises three separate shutters, namely a first shutter configured for allowing light to pass towards the image sensor, a second shutter configured for allowing light to pass towards the image sensor during the second acquisition period, and a third shutter configured for allowing light to pass towards the image sensor during the third acquisition period.

The invention also relates to a method of determining the physiological state of the occupant by photoplethysmography.

The method can also include the following steps:

the pulsed light source emits a train of light pulses towards the occupant, this action corresponding to a first step;

simultaneously, the shutter opens to allow light to pass towards the image sensor, this light comprising a component due to ambient illumination and a component due to the light pulse emitted by the pulsed light source, this action corresponding to a second step;

at the end of the first acquisition period, the pulsed light source is inactivated, this action corresponding to a third step;

the shutter opens to allow light to pass towards the image sensor during a second acquisition period, this light comprising a component due to ambient illumination and possibly a component due to the light pulse emitted previously by the pulsed light source, this action corresponding to a fourth step;

if the image acquisition device comprises a plurality of shutters, the method comprises a fifth step in which the second shutter is reclosed and the third shutter is opened;

the shutter opens to allow light to pass towards the image sensor during a third acquisition period, this light comprising a component due to ambient illumination, but more of a component due to the light pulse emitted previously by the pulsed light source, this action corresponding to a sixth step;

at the end of the third acquisition period, the shutter is reclosed; this action corresponds to a seventh step;

the processing unit subtracts the component due to ambient illumination, contained in the light received by the image sensor during the third acquisition period, from the light received by the image sensor during the first and second acquisition periods, in order to isolate the component due to the light pulse emitted by the pulsed light source in the images acquired by the image acquisition device during the first and second acquisition periods, this action corresponding to an eighth step;

on the basis of said images, the processing unit determines one or more physiological parameters of the occupant by photoplethysmography, this action corresponding to a ninth step;

on the basis of the physiological parameter, the processing unit determines the physiological state of the occupant by photoplethysmography, this action corresponding to a tenth step.

Further advantages and features of the invention will become more clearly apparent from reading the following description, given by way of illustrative and nonlimiting example, and the appended drawings, in which.

Figure 3A:
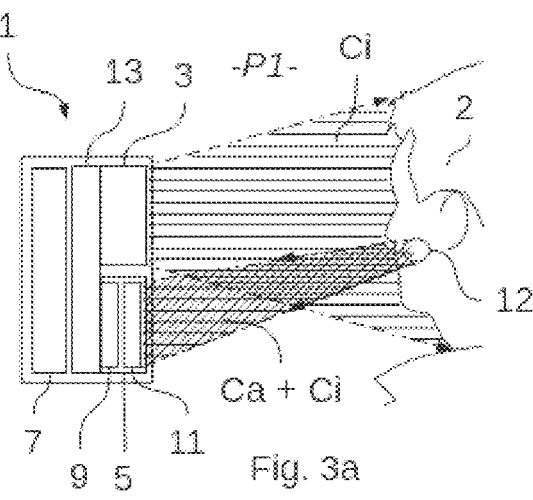
FIG. 3a is a figure similar to FIG. 1, and shows schematically the state of the monitoring system during a first acquisition period.
Figure 3B:
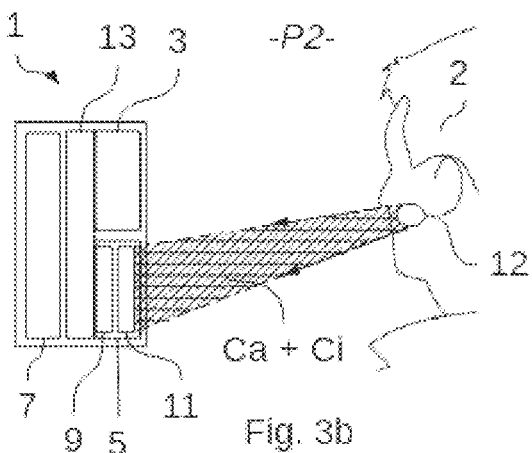
Figure 3C:
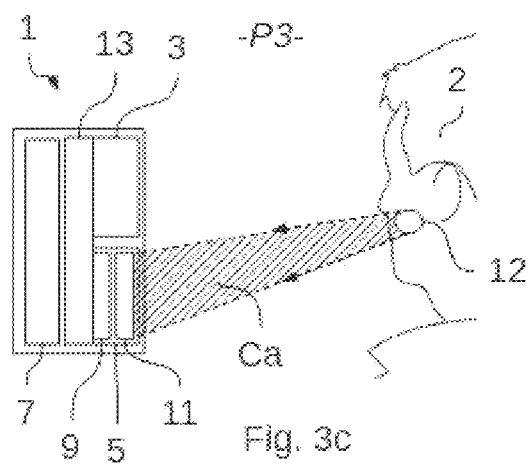
Figure 4:
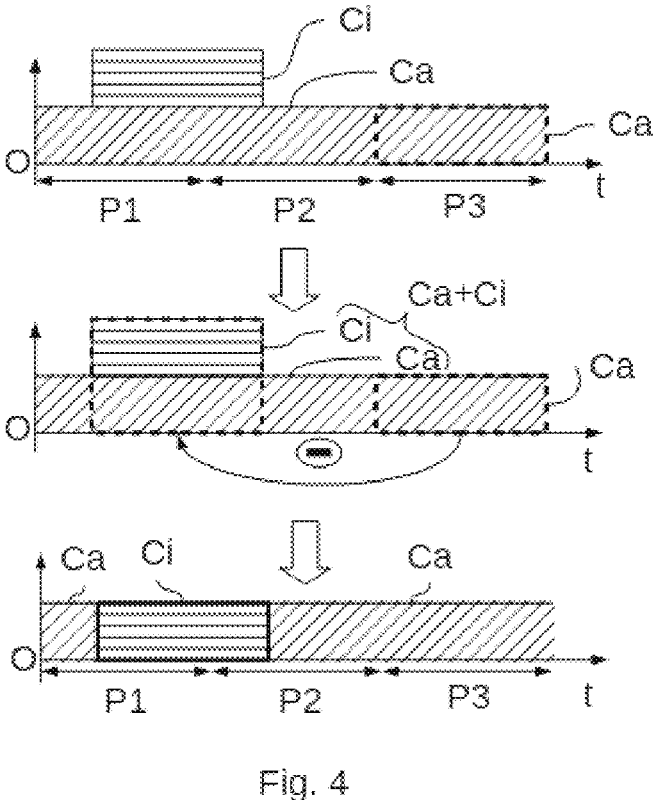
Figure 5:
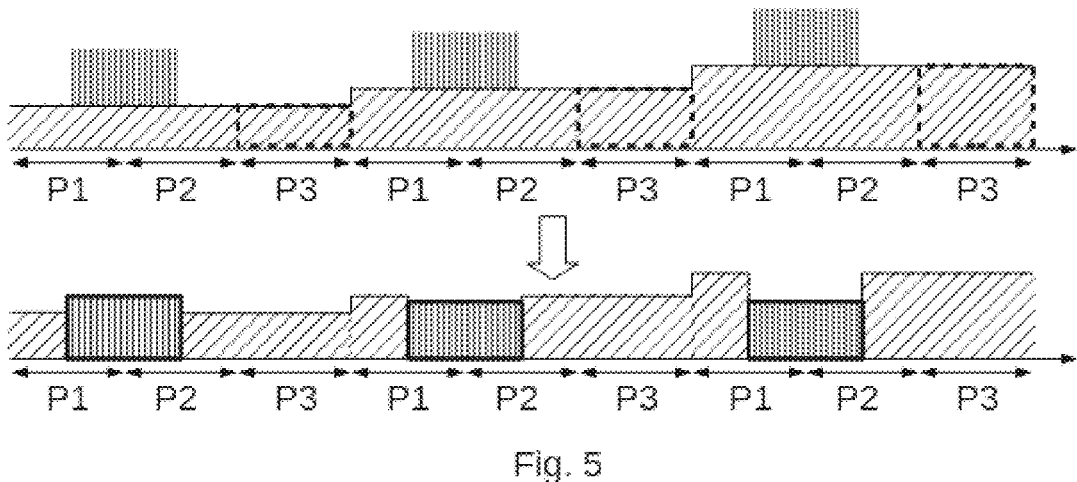
Figure 7:
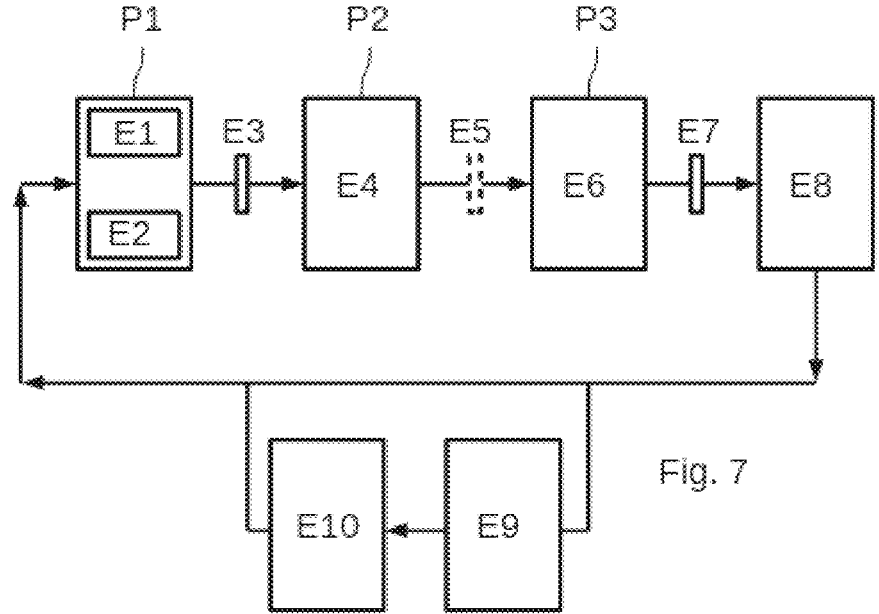

FIG. 3b is a figure similar to FIG. 3a, and shows schematically the state of the monitoring system during a second acquisition period, FIG. 3c is a figure similar to FIGS. 3a and 3b, and shows schematically the state of the monitoring system during a third acquisition period, FIG. 4 shows schematically some steps of the process carried out by the processing unit after the third acquisition period, FIG. 5 is a figure similar to FIG. 4, and shows some steps of the process carried out by the processing unit over a longer time interval, FIG. 6a shows a schematic view of a second embodiment of the system for monitoring an occupant during a first acquisition period, FIG. 6b is a figure similar to the preceding figure, and shows schematically the state of the monitoring system of FIG. 6a during a second acquisition period, FIG. 6c is a figure similar to the preceding two figures, and shows schematically the state of the monitoring system of FIGS. 6a and 6b during a third acquisition period, and FIG. 7 is a flow diagram showing the steps of a method for determining the physiological state of the occupant by photoplethysmography.

In these figures, identical elements bear the same reference numerals. The elements shown are not all depicted on the same scale: some components of the monitoring system have been enlarged for the sake of clarity.

The following embodiments are examples. Although the description refers to one or more embodiments, this does not necessarily mean that each reference relates to the same embodiment, or that the features apply only to a single embodiment. Individual features of different embodiments may also be combined or interchanged to provide other embodiments.

In the description, certain elements may be indexed, such as first element or second element, for example. In this case, the index is simply used to differentiate and denote elements that are similar but not identical. This indexing does not imply that one element takes priority over another and such denominations can easily be interchanged without departing from the scope of the present description. This indexing does not imply an order in time either.

Figure 1:
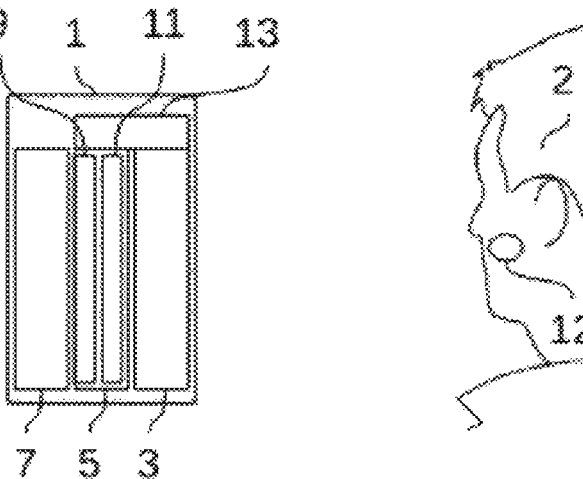
FIG. 1 shows a schematic view of a system for monitoring an occupant according to a first embodiment.

FIG. 1 shows schematically a first embodiment of a monitoring system 1 with an occupant 2 of a motor vehicle (the motor vehicle is not shown in FIG. 1). The occupant 2 is, for example, the driver of the motor vehicle or a passenger. There may be more than one occupant, forming a group comprising a driver and one or more passengers, for example. The monitoring system 1 comprises, more particularly, a pulsed light source 3, an image acquisition device 5 such as a time of flight camera, and a processing unit 7.

The pulsed light source 3 is configured for emitting a train of light pulses, particularly in the infrared and therefore invisibly to the human eye, towards the occupant 2. The monitoring system 1 is therefore arranged in the interior of the motor vehicle, in such a way that the pulsed light source 3 enables the face of the occupant 2 to be illuminated more particularly, and in such a way that the images acquired by the image acquisition device 5 comprise some or all of the face of the occupant 2. The monitoring system 1 is, for example, arranged within the dashboard. There are other feasible locations, for example in the structure of the interior mirror or the roof of the interior more generally.

According to the embodiment of the monitoring system 1 shown schematically in FIG. 1, the pulsed light source 3 is located outside the enclosure of the structure of the image acquisition device 5. According to another embodiment of the monitoring system, the pulsed light source 3 may be included within the structure of the image acquisition device 5.

The pulsed light source 3 is, for example, an infrared radiation source. It may, notably, take the form of a light-emitting diode (LED) or a laser diode. The wavelength of the train of light pulses emitted by such a light source is, for example, within a range extending, notably, from 850 nm to 940 nm. Advantageously, such infrared radiation is invisible to the human eye. The risk of distracting the attention of the occupant 2 during the emission of the train of light pulses is therefore relatively small.

The image acquisition device 5 comprises an image sensor 9, for example a photographic sensor such as a CMOS or CCD sensor. The image acquisition device 5 also comprises a shutter 11, configured for allowing light to pass towards the image sensor 9; this shutter 11 may be mechanical or electrical. According to an embodiment of the image acquisition device 5 which is not illustrated, this device may comprise a plurality of image sensors 9.

The images acquired by the image acquisition device 5 are to be processed by the processing unit 7 which is configured for determining one or more physiological parameters of the occupant 2 on the basis of said images. The determination of the physiological parameter(s) is carried out by means of remote photoplethysmography. The methods of remote photoplethysmography are known and will not be detailed in this description. The physiological parameter may be the heart rate, the respiration rate or the arterial blood oxygen saturation.

Figure 2:
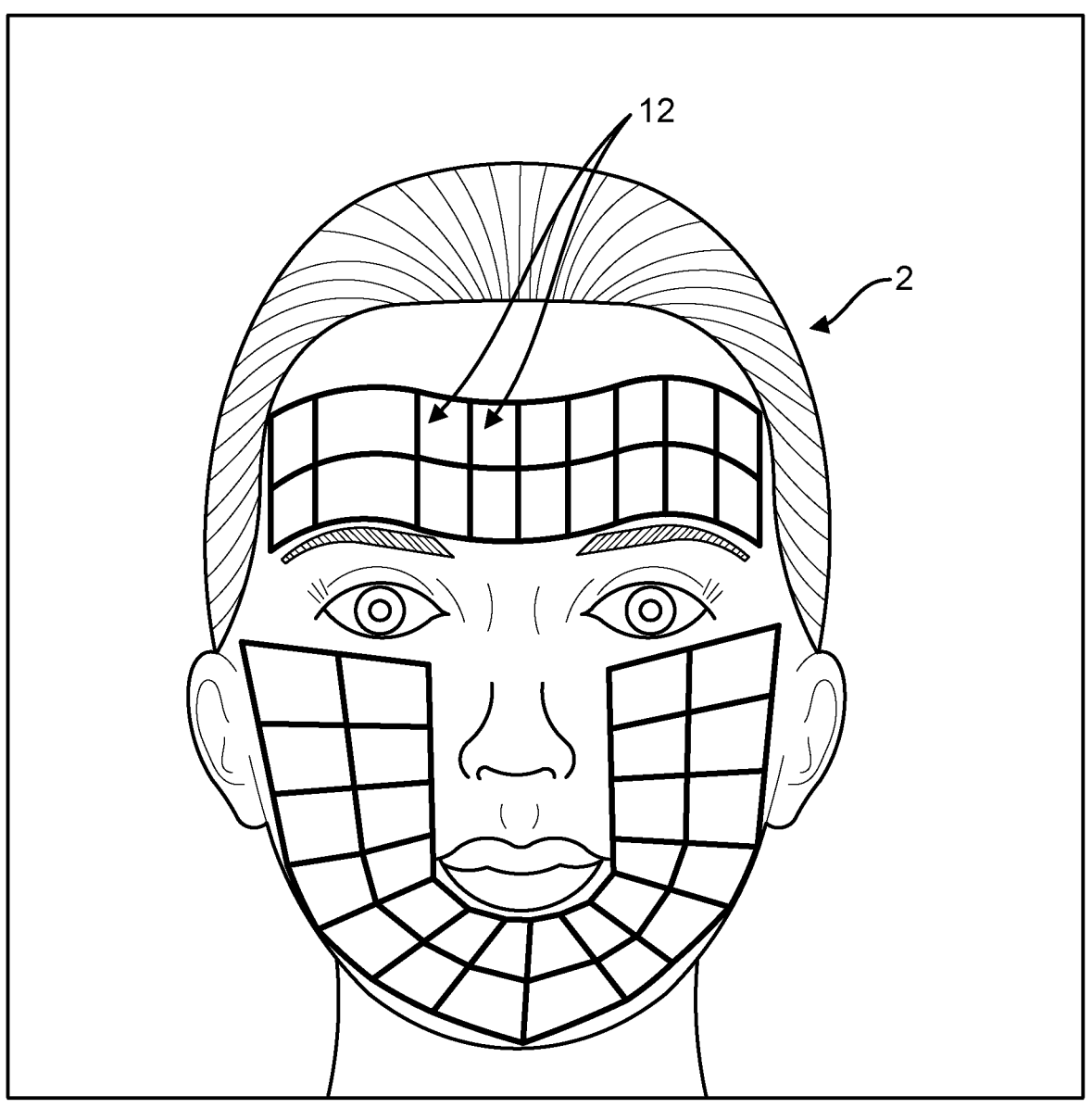
FIG. 2 is an illustration indicating the regions of interest on the face of an occupant.

More particularly, the monitoring system 1 may be configured for selecting one or more regions of interest 12 on the face of the occupant 2, in order to enable the physiological parameter to be determined by remote photoplethysmography in a non-intrusive manner. A region of interest 12 may, notably, denote part or all of the forehead, the cheeks or the chin of the occupant 2, as indicated by way of example in FIG. 2.

It should be noted that the image acquisition device 5 is a time of flight (ToF) camera. With this type of camera it is possible to acquire simultaneously information on the luminous intensity and information on the distance between the occupant 2 and the sensor 9 of the image acquisition device 5 of the monitoring system 1. A time of flight camera is thus capable of reconstructing the filmed scene in three dimensions in a minimum of time, thus facilitating real-time monitoring of the movements of the occupant 2.

More particularly, the image sensor 9 is configured for producing a depth map of the face of the occupant 2 on the basis of the images acquired by the image acquisition device 5. This depth map makes it possible, more particularly, to evaluate the position of the head of the occupant 2 and to locate the movement of the region(s) of interest 12 on the face of the occupant 2 when he is required to move, as for example when he turns his head to reverse the vehicle. In fact, the movements of the head of the occupant 2 may complicate the identification of the region(s) of interest 12 in the images of the face of the occupant 2 to be processed by the processing unit 7.

This monitoring system 1 also makes it possible to avoid another difficulty identified in the introduction, namely the changes in ambient illumination within the interior of the motor vehicle. The virtually incessant variation of light inside and around the motor vehicle may cause the ambient illumination to change frequently, which may affect the intensity in the images acquired by the image acquisition device 5 of the monitoring system 1. In other words, the face of the occupant 2 is not illuminated uniformly over time; a component Ca due to the ambient illumination in the images is variable over time. It is therefore essential to obviate this component Ca due to the ambient illumination, which interferes with said images and which may perturb the determination of the physiological parameter by remote photoplethysmography carried out by the processing unit 7.

With this in mind, the acquisition of said images takes place cyclically, and each cycle comprises three periods, referred to as the "first acquisition period P1", the "second acquisition period P2" and the "third acquisition period P3" in the remainder of this description. The second acquisition period P2 is initiated outside the first acquisition period P1. Similarly, the third acquisition period P3 is initiated outside the first acquisition period P1 and the second acquisition period P2. These three acquisition periods P1, P2, P3 may, notably, succeed each other, in which case the second acquisition period P2 starts at the moment when the first acquisition period P1 finishes, and the third acquisition period P3 starts at the moment when the second acquisition period P2 finishes.

FIGS. 3a, 3b and 3c show schematically, respectively, the actions of the monitoring system 1 during the first acquisition period P1, the second acquisition period P2 and the third acquisition period P3.

With reference to FIG. 3a, the first acquisition period P1 is marked by two events taking place simultaneously: the monitoring system 1 is configured in such a way that the pulsed light source 3 emits a light pulse towards the occupant 2, as represented, notably, by the hatched area between the two arrows in broken lines pointing towards the occupant 2. The light emitted by the pulsed light source 3 is represented by horizontal hatching. Simultaneously, the shutter 11 is opened to allow light to pass from the occupant 2 to the image sensor 9 of the acquisition device 5 of the monitoring system 1 during the first acquisition period P1, as represented more particularly by the hatched area between the two arrows pointing to the rectangle representing the shutter 11.

To ensure that these two phenomena take place simultaneously, the monitoring system 1 may comprise a control unit 13 (shown schematically in FIGS. 1, 3*a*, 3*b* and 3*c*) which is configured for synchronizing the start of the train of light pulses emitted by the pulsed light source 3 with the opening of the shutter 11 at the start of the first acquisition period P1. Additionally, this control unit 13 can also be configured for controlling the opening and closing of the shutter 11.

The light pulse emitted by the pulsed light source 3 completes a transit over a time which is a function of the distance between the object that it illuminates and the image sensor 9 of the image acquisition device 5 of the monitoring system 1. Thus the transit time of a light pulse reflected from an object placed near the image sensor 9 and the pulsed light source 3 will be shorter than that of a light pulse reflected from an object placed farther away. Since the speed of light is known, this transit time may be used to calculate the distance between, notably, the regions of interest 12 of the face of the occupant 2 and the image sensor 9 of the image acquisition device 5 of the monitoring system 1.

Depending on the distance covered by the light pulse and the duration of the first acquisition period P1, the light emitted by the pulsed light source 3 and reflected by the occupant 2 does not necessarily have time to pass through the shutter 11 of the image acquisition device 5 before the end of the first acquisition period P1, and for this reason there is a second acquisition period P2 following the first. The sensor 11 is open during the second acquisition period P2 to allow the light to pass all the way to the sensor 9 of the image acquisition device 5. Thus part of the light pulse emitted by the pulsed light source 3 and reflected by the occupant 2 may need to pass through the shutter 11 during this second acquisition period P2 in order to avoid a potential loss of data. This "delayed" part of the light received by the image sensor 9 of the image sensor 5 corresponds, notably, to the light rays that are reflected from objects placed at a greater distance from the pulsed light source 3.

With reference to FIG. 3*b* which represents the state of the monitoring system 1 during the second acquisition period P2, the pulsed light source 3 is inactive: it no longer emits any light pulses towards the occupant 2. Like the light passing through the shutter 11 towards the sensor 9 during the first acquisition period P1, the light passing through the shutter 11 towards the sensor 9 during the second acquisition period P2 also comprises one component Ca due to the ambient illumination and one component Ci due to the light pulse. In FIGS. 3*a* and 3*b*, the component Ci due to the light pulse in the light reflected by the region(s) of interest 12 of the face of the occupant 2 towards the shutter 11 is represented by an area with horizontal hatching, and the component Ca due to ambient illumination in the light reflected by the region(s) of interest 12 of the face of the occupant 2 towards the shutter 11 is represented by oblique hatching in the same area.

If the pulsed light source 3 emits a light pulse in the infrared domain, the light perceived by the image sensor 9 during the first and second acquisition periods P1, P2 therefore comprises a visible light component and an infrared light component.

The duration of each of the first acquisition period P1 and the second acquisition period P2 is at least equal to the duration of a light pulse emitted by the pulsed light source

3. According to one embodiment of the monitoring system 1, the duration of one pulse of the train of light pulses emitted by the pulsed light source 3 is equal to the duration of the first acquisition period P1. The pulsed light source 3 is inactivated at the end of the first acquisition period P1, and remains inactive during the second and third acquisition periods P2 and P3. The shutter 11, for its part, allows light to pass towards the image sensor 9 during each of the three acquisition periods P1, P2 and P3. Additionally, the durations of the first, second and third acquisition periods P1, P2, P3 may be identical to each other.

The duration of the light pulse, the duration of the first, second and third acquisition periods P1, P2 and P3, and the distance between the occupant 2 and the monitoring system 1 are such that the light received by the image sensor 9 during the third acquisition period P3 comprises no component Ci due to the light pulse emitted by the pulsed light source 3. In other words, only the ambient light is received by the image sensor 9 during the third acquisition period P3. In FIG. 3*c*, the component Ca due to the ambient illumination is represented by oblique hatching in the area representing the light reflected by the region(s) of interest 12 of the face of the occupant 2 towards the shutter 11. There is no horizontal hatching in this area, since this light has no component Ci due to the light pulse emitted by the pulsed light source 3.

The respective durations of the three acquisition periods P1, P2, P3 are very short, being for example less than 50 ns, and more particularly equal to 20 ns. They are so short that the change of ambient illumination on the face of the occupant 2 is negligible over this time interval; that is to say, the component Ca due to ambient illumination in the light received by the image sensor 9 is considered to be identical in all the images acquired by the image acquisition device 5 during these three acquisition periods P1, P2, P3 belonging to the same cycle.

In order to obviate the component Ca due to ambient illumination in the images acquired by the image acquisition device 5 during the first acquisition period P1 and the second acquisition period P2, the processing unit 7 is configured for subtracting this component Ca from some or all of said images, with the aim of isolating the component Ci due to the light pulse emitted by the pulsed light source 3. This operation is shown schematically in FIG. 4. This figure shows a plurality of timelines having a time axis t, the beginning of which is marked by the origin O. The time axis t is divided into three segments of the same length, indicated by the double arrows. Each double arrow represents an acquisition period P1, P2, P3. The rectangular blocks above these double arrows represent the light received by the image sensor 9 during these three acquisition periods P1, P2 and P3. Since the component Ca due to ambient illumination is considered to be constant during the three acquisition periods P1, P2, P3 of a single cycle, this component Ca is represented here by a first rectangular block comprising oblique hatching. The total length of this first block is equal to the sum of the lengths of the three double arrows.

A second block with a length equal to a single double arrow lies above the first block. The horizontal hatching inside the second block represent the component Ci due to the light pulse emitted by the pulsed light source 3. The offset between the start of this second block and the origin O is due to the transit time of the light pulse emitted by the pulsed light source 3.

The subtraction operation performed by the processing unit 7 takes place as follows: the processing unit 7 locates the component Ca due to ambient illumination in the images acquired by the image acquisition device 5 during the third acquisition period P3, as indicated by the bold broken lines on the first timeline. The value of this component Ca is subtracted from the amount of light received by the image sensor 9, during which process said image sensor 9 also receives the component Ci due to the light pulse reflected by the region(s) of interest 12 of the face of the occupant 2, this being shown on the second timeline positioned below the first timeline. After this subtraction operation, the processing unit 7 therefore focuses on the images which comprise only the component Ci, in order to apply a photoplethysmography method to them so as to determine a physiological parameter of the occupant 2. This last step is represented by the frame marked out in thick lines on the third timeline of FIG. 4.

FIG. 5 shows two time axes similar to those of FIG. 4. These time axes represent three consecutive cycles of three acquisition periods P1, P2 and P3 which follow each other. The component Ca due to ambient illumination is specific to each cycle, as represented by the different sizes of the blocks Ca1, Ca2 and Ca3 with the oblique hatching. Thus FIG. 5 shows the repetition of the subtraction operation performed by the processing unit 7 in one cycle after another.

The processing unit 7 is therefore configured for subtracting the component Ca due to ambient illumination from the light received by the sensor 9 of the image acquisition device 5 for the images acquired during the first and second acquisition periods P1 and P2. Thus the images acquired by the image acquisition device 5 during the first and second acquisition periods P1 and P2 are no longer interfered with by the component Ca due to ambient illumination, and this increases the effectiveness of the image processing carried out by the processing unit 7 in the context of the determination of the physiological parameter by remote photoplethysmography.

The processing unit 7 is also configured for defining the physiological state of the occupant 2 on the basis of the physiological parameter. The processing unit 7 may, for example, compare the value of the physiological parameter(s) with one or more predetermined thresholds. By way of example, we may consider the case where the occupant 2 monitored by the monitoring system 1 is also the driver of the motor vehicle. In this example, the physiological parameter is the heart rate. If this parameter is above a predetermined maximum threshold or below a predetermined minimum threshold within the processing unit 7, it is possible that the physiological state of the occupant 2 will not allow him to drive.

The monitoring system 1 may, notably, be configured for emitting, for example, an audible signal or any other form of warning if the physiological parameter(s) do not meet the predetermined criteria within the processing unit 7. An audible signal may warn the occupant of a potential danger such as driving in a state of fatigue.

Since the respective durations of the three acquisition periods P1, P2 and P3 are very short, the acquisition cycle must be repeated many times in order to collect enough data for the purpose of determining the physiological parameter. This process requires a degree of reactivity in the components of the monitoring system 1.

To this end, the monitoring system 1 may comprise a number of shutters 111, 112 and 113. According to another embodiment of the image acquisition device 5, the image acquisition device 5 may comprise a first shutter 111 configured for allowing light to pass towards the image sensor 9 during the first acquisition period P1, a second shutter 112 configured for allowing light to pass towards the image sensor 9 during the second acquisition period P2, and a third shutter 113 configured for allowing light to pass towards the image sensor 9 during the third acquisition period P3, as shown in the images 5a, 5b and 5c. Thus the first shutter 111 is opened at the start of the first acquisition period P1 and reclosed at the end of the first acquisition period P1, the second shutter 112 is opened at the start of the second acquisition period P2 and reclosed at the end of the second acquisition period P2, and the same principle is followed for the third shutter 113 and the third acquisition period P3. The operation of this second embodiment of the monitoring system 1 is very similar to that of the first embodiment, whence the similarity between FIGS. 6a, 6b and 6c and FIGS. 3a, 3b and 3c respectively.

In this particular embodiment, the control unit 13 may be configured for controlling the opening and closing of the first, second and third shutters 111, 112 and 113 in sequence. In other words, the closing of the first shutter 111 coincides with the opening of the second shutter 112, and the closing of the second shutter 112 coincides with the opening of the third shutter 113. This particular design of the monitoring system 1 may make it possible to reduce the stress on the different shutters 111, 112 and 113, which may result in an increased service life of the monitoring system 1.

With reference to the flow diagram in FIG. 7, a method of determining the physiological state of the occupant 2 by photoplethysmography is detailed in the remainder of the description. This method makes use of a monitoring system 1 as described above. The method comprises a plurality of steps E1, E2, E3, E4, E5, E6, E7, E8, E9 and E10.

Steps E1 and E2 take place at the same time during the first acquisition period P1. For step E1, the pulsed light source 3 emits a train of light pulses towards the occupant 2, while for step E2, which takes place simultaneously, the shutter 11, or the first shutter 111, is opened to allow light to pass towards the image sensor 9. This light comprises a component Ca due to ambient illumination and a component Ci due to the light pulse emitted by the pulsed light source 3.

At the end of this first acquisition period P1, the pulsed light source 3 is inactivated, this event corresponding to step E3. Step E3 also marks the end of the first acquisition period P1 and the start of the second acquisition period P2. If the image acquisition device 5 comprises a plurality of shutters, this step E3 is also marked by the closing of the first shutter 111 and the opening of the second shutter 112.

In step E4, the shutter 11 or the second shutter 112 opens to allow light to pass towards the image sensor 9 during the second acquisition period P2, this light comprising a component Ca due to ambient illumination and possibly a component Ci due to the light pulse emitted previously by the pulsed light source 3.

Step E5 marks the end of the second acquisition period P2 and the start of the third acquisition period P3. If the image acquisition device 5 comprises a plurality of shutters 111, 112, 113, the step E5 also corresponds to the moment when the second shutter 112 is reclosed and the third shutter 113 is opened.

In step E6, the shutter 11 or 113 opens to allow light to pass towards the image sensor 9 during the third acquisition period P3, this light comprising a component Ca due to ambient illumination, but more of the component Ci due to the light pulse emitted previously by the pulsed light source 3.

In step E7, at the end of the third acquisition period P3, the shutter 11 or the third shutter 113 is reclosed.

In step E8, the processing unit 7 subtracts the component Ca due to ambient illumination, contained in the light received by the image sensor 9 during the third acquisition period P3, from the light received by the image sensor 9 during the first and second acquisition periods P1, P2, in order to isolate the component Ci due to the light pulse emitted by the pulsed light source 3 in the images acquired by the image acquisition device 5 during the first and second acquisition periods P1, P2.

In step E9, the processing unit 7 determines a physiological parameter of the occupant 2 by photoplethysmography on the basis of said images. In step E10, the processing unit 7 defines the physiological state of the occupant 2 by photoplethysmography on the basis of the physiological parameter. It may not be necessary to repeat steps E9 and E10 for each cycle. In other words, it would be feasible to repeat steps E1 to E8 several times in succession before initiating steps E9 and E10. For example, the processing unit 7 of the monitoring system 1 may be configured for selecting the images worth processing for the method of calculating the physiological state of the occupant 2, by removing, for example, the images in which the occupant 2 is not orientated with his face towards the monitoring system 1, as in the case where the occupant is a driver and turns his head in order to reverse his vehicle, since these images cannot be used to determine a physiological parameter of the occupant 2 by photoplethysmography in a reliable manner.

The invention claimed is:

1. A system for monitoring an occupant of a motor vehicle, the system comprising:
   a pulsed light source configured for emitting a train of light pulses towards the occupant, the train of light pulses comprising a first light pulse;
   an image acquisition device configured to acquire one or more images, the image acquisition device comprising an image sensor and a first shutter configured for allowing a reflected light to pass towards the image sensor during a first acquisition period in which the pulsed light source emits the first light pulse, wherein the image acquisition device further comprises a time-of-flight camera, a second shutter configured for allowing the reflected light to pass towards the image sensor during a second acquisition period in which the pulsed light source is inactive, and a third shutter configured for allowing the reflected light to pass towards the image sensor during a third acquisition period, the third acquisition period being initiated outside the first and the second acquisition periods, the pulsed light source being inactive during the third acquisition period,
   wherein the second acquisition period is initiated outside the first acquisition period,
   wherein a duration of each of the first and the second acquisition periods is at least equal to the duration of the first light pulse emitted by the pulsed light source,
   wherein the reflected light received by the image sensor in the first acquisition period and the second acquisition period comprises an ambient light component due to ambient illumination and an emitted light component due to at least one light pulse of the train of light pulses emitted by the pulsed light source; and
   a processing unit configured for determining at least one physiological parameter of the occupant by photoplethysmography based on one or more images acquired by the image acquisition device, and for defining a physiological state of the occupant based on the at least one physiological parameter, wherein the reflected light received by the image sensor in the third acquisition period comprises the ambient light component due to the ambient illumination, and
wherein the processing unit is configured for subtracting the ambient light component due to the ambient illumination from the reflected light received by the image sensor during the first and the second acquisition periods, in order to isolate the emitted light component due to the first light pulse emitted by the pulsed light source in the one or more images acquired by the image acquisition device during the first and the second acquisition periods.

2. The system according to claim 1, wherein the duration of each of the first, second and third acquisition periods is equal to 20 ns.

3. The system according to claim 2, wherein the durations of the first, second and third acquisition periods are identical to each other.

4. The system according to claim 1, wherein the duration of one pulse of the train of light pulses emitted by the pulsed light source is equal to the duration of the first acquisition period.

5. The system according to claim 1, further comprising a control unit configured for synchronizing a start of the train of light pulses emitted by the pulsed light source with an opening of the first shutter at a start of the first acquisition period.

6. The system according to claim 5, wherein the control unit is configured for controlling the opening and a closing of the first shutter.

7. The system according to claim 1, wherein the processing unit is configured to select a region of interest on a face of the occupant to enable the at least one physiological parameter to be determined.

8. The system according to claim 1, wherein the image sensor is configured for producing a depth map of a face of the occupant based on the one or more images acquired by the image acquisition device.

9. A method for determining the physiological state of the occupant of the motor vehicle by the photoplethysmography, the method making use of the system according to claim 1, wherein the method comprises:
   emitting the train of light pulses towards the occupant using the pulsed light source and, simultaneously, opening the first shutter to allow the reflected light to pass towards the image sensor,
   wherein the reflected light comprises the ambient light component due to the ambient illumination and the emitted light component due to the first light pulse emitted by the pulsed light source;
   inactivating the pulsed light source and closing the first shutter at an end of the first acquisition period;
   opening the second shutter to allow the reflected light to pass towards the image sensor during the second acquisition period, the reflected during the second acquisition period light comprising the ambient light component due to the ambient illumination and the emitted light component due to the first light pulse emitted by the pulsed light source;
   closing the second shutter at an end of the second acquisition period;
   opening the third shutter to allow the reflected light to pass towards the image sensor during the third acquisition period, the reflected light during the third acquisition period comprising the ambient light component due to the ambient illumination;

closing the third shutter at an end of the third acquisition period;

subtracting, using the processing unit, the ambient light component due to the ambient illumination, contained in the reflected light received by the image sensor during the third acquisition period, from the reflected light received by the image sensor during the first and the second acquisition periods to isolate the emitted light component due to the first light pulse emitted by the pulsed light source in the one or more images acquired by the image acquisition device during the first and the second acquisition periods;

determining, using the processing unit, the at least one physiological parameter of the occupant by the photoplethysmography based on the one or more images acquired by the image acquisition device during the first and the second acquisition periods; and determining, using the processing unit, the physiological state of the occupant by the photoplethysmography based on the at least one physiological parameter.

10. The system according to claim 1, wherein the first shutter is opened at a start of the first acquisition period and closed at an end of the first acquisition period, wherein the second shutter is opened at a start of the second acquisition period and closed at an end of the second acquisition period, and wherein the third shutter is opened at a start of the third acquisition period and closed at an end of the third acquisition period.

* * * * *